(12) United States Patent
Massarwa et al.

(10) Patent No.: US 11,113,899 B1
(45) Date of Patent: Sep. 7, 2021

(54) CORRECTING ANATOMICAL MAPS

(71) Applicant: BIOSENSE WEBSTER (ISRAEL) LTD., Yokneam (IL)

(72) Inventors: Fady Massarwa, Baka Al Gharbiyya (IL); Assaf Cohen, Kiryat Bialik (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 17/007,493

(22) Filed: Aug. 31, 2020

(51) Int. Cl.
| | | |
|---|---|---|
| G06T 19/20 | (2011.01) | |
| G06T 17/00 | (2006.01) | |
| A61B 5/339 | (2021.01) | |
| A61B 5/283 | (2021.01) | |

(52) U.S. Cl.
CPC .............. *G06T 19/20* (2013.01); *A61B 5/339* (2021.01); *G06T 17/00* (2013.01); *A61B 5/283* (2021.01); *G06T 2200/24* (2013.01); *G06T 2210/41* (2013.01); *G06T 2210/56* (2013.01); *G06T 2219/2008* (2013.01); *G06T 2219/2021* (2013.01)

(58) Field of Classification Search
None
See application file for complete search history.

(56) References Cited

U.S. PATENT DOCUMENTS

| | | |
|---|---|---|
| 5,391,199 A | 2/1995 | Ben Haim |
| 5,443,489 A | 8/1995 | Ben Haim |
| 5,558,091 A | 9/1996 | Acker |
| 6,177,792 B1 | 1/2001 | Govari |
| 6,690,963 B2 | 2/2004 | Ben Haim |
| 6,788,967 B2 | 9/2004 | Ben Haim |
| 6,968,299 B1 * | 11/2005 | Bernardini ............ G06F 17/175 345/424 |
| 7,103,202 B2 * | 9/2006 | Bruijns .................... G06T 7/62 382/128 |
| 8,456,182 B2 | 6/2013 | Bar-Tal |
| 2005/0147297 A1 * | 7/2005 | McLaughlin ........... G06T 7/143 382/171 |
| 2009/0148012 A1 | 6/2009 | Altmann |

(Continued)

OTHER PUBLICATIONS

Villard B, Grau V, Zacur E. Surface Mesh Reconstruction from Cardiac MRI Contours. Journal of Imaging. 2018; 4(1): 16 (Year: 2018).*

(Continued)

*Primary Examiner* — Ryan M Gray (57) ABSTRACT

A system includes a display and a processor. The processor is configured to compute a point P' on a virtual surface of a point cloud representing an anatomical volume, by projecting another point P, which corresponds to a location on an anatomical surface of the anatomical volume, onto the virtual surface. The processor is further configured to define a virtual sphere centered on a virtual line joining P to P' such that P lies on a spherical surface of the virtual sphere, and to expand the point cloud throughout the virtual sphere or exclude the virtual sphere from the point cloud. The processor is further configured to regenerate the virtual surface such that, by virtue of having expanded the point cloud or excluded the virtual sphere, P lies on the virtual surface, and to display the regenerated virtual surface on the display. Other embodiments are also described.

20 Claims, 4 Drawing Sheets

(56) References Cited

U.S. PATENT DOCUMENTS

| | | | |
|---|---|---|---|
| 2011/0044526 A1* | 2/2011 | Liu | G06T 7/11 |
| | | | 382/132 |
| 2013/0030280 A1* | 1/2013 | Govari | A61B 5/055 |
| | | | 600/410 |
| 2013/0138404 A1* | 5/2013 | Carbonera | G06T 17/205 |
| | | | 703/2 |
| 2013/0281813 A1* | 10/2013 | Markowitz | A61B 5/06 |
| | | | 600/382 |
| 2014/0168073 A1* | 6/2014 | Chizeck | G06F 3/016 |
| | | | 345/156 |
| 2015/0117708 A1* | 4/2015 | Guigues | G06T 7/246 |
| | | | 382/103 |
| 2018/0240282 A1* | 8/2018 | Voth | G06T 17/00 |
| 2018/0279895 A1* | 10/2018 | Relan | G06T 11/206 |
| 2020/0197095 A1* | 6/2020 | Harlev | A61B 34/10 |
| 2020/0211713 A1* | 7/2020 | Shadforth | A61B 5/7257 |
| 2020/0289025 A1* | 9/2020 | Dichterman | A61B 5/6852 |
| 2021/0090215 A1* | 3/2021 | Ben-Haim | G06T 3/4038 |

OTHER PUBLICATIONS

Chen, Zhong, et al. "Adaptive Meshing Based on the Multi-level Partition of Unity and Dynamic Particle Systems for Medical Image Datasets." International Journal Bioautomation 22.3 (2018): 229. (Year: 2018).*

Bernardini, Fausto, et al., "The ball-pivoting algorithm for surface reconstruction," *IEEE transactions on visualization and computer graphics* 5.4 (1999): 349-359.

* cited by examiner

CORRECTING ANATOMICAL MAPS

FIELD OF THE INVENTION

The present invention relates to the field of anatomical mapping.

BACKGROUND

United States Patent Application Publication No. 2009/0148012 to Altmann et al. describes a method of medical imaging, including creating an anatomical map of an inner wall of a cavity in a body of a subject by inserting a probe into the body and collecting data using the probe. A three-dimensional (3-D) contour is delineated in a 3-D image of the cavity based on the map.

SUMMARY OF THE INVENTION

There is provided, in accordance with some embodiments of the present invention, a system including a display and a processor. The processor is configured to compute a point P' on a virtual surface of a point cloud representing an anatomical volume, by projecting another point P, which corresponds to a location on an anatomical surface of the anatomical volume, onto the virtual surface. The processor is further configured to define a virtual sphere centered on a virtual line joining P to P' such that P lies on a spherical surface of the virtual sphere. The processor is further configured to perform an operation selected from the group of operations consisting of: expanding the point cloud throughout the virtual sphere, and excluding the virtual sphere from the point cloud. The processor is further configured to regenerate the virtual surface, subsequently to performing the operation, such that, by virtue of having performed the operation, P lies on the virtual surface, and to display the regenerated virtual surface on the display.

In some embodiments, the processor is configured to regenerate the virtual surface by applying a ball-pivoting algorithm (BPA) with a ball radius r to the point cloud, and the processor is configured to define the sphere such that a radius R of the sphere is at least 2r.

In some embodiments, R=2r.

In some embodiments, the processor is further configured to identify P in response to an input from a user.

In some embodiments, the input indicates that an intrabody probe is at the location.

In some embodiments, the input includes a selection of P from a display of the point cloud.

In some embodiments, the anatomical volume includes at least part of a chamber of a heart.

There is further provided, in accordance with some embodiments of the present invention, a method including, using a processor, computing a point P' on a virtual surface of a point cloud representing an anatomical volume, by projecting another point P, which corresponds to a location on an anatomical surface of the anatomical volume, onto the virtual surface. The method further includes defining a virtual sphere centered on a virtual line joining P to P' such that P lies on a spherical surface of the virtual sphere. The method further includes performing an operation selected from the group of operations consisting of: expanding the point cloud throughout the virtual sphere, and excluding the virtual sphere from the point cloud. The method further includes, subsequently to performing the operation, regenerating the virtual surface such that, by virtue of having performed the operation, P lies on the virtual surface.

There is further provided, in accordance with some embodiments of the present invention, a computer software product including a tangible non-transitory computer-readable medium in which program instructions are stored. The instructions, when read by a processor, cause the processor to compute a point P' on a virtual surface of a point cloud representing an anatomical volume, by projecting another point P, which corresponds to a location on an anatomical surface of the anatomical volume, onto the virtual surface. The instructions further cause the processor to define a virtual sphere centered on a virtual line joining P to P' such that P lies on a spherical surface of the virtual sphere. The instructions further cause the processor to perform an operation selected from the group of operations consisting of: expanding the point cloud throughout the virtual sphere, and excluding the virtual sphere from the point cloud. The instructions further cause the processor to regenerate the virtual surface, subsequently to performing the operation, such that, by virtue of having performed the operation, P lies on the virtual surface.

There is further provided, in accordance with some embodiments of the present invention, a system including an input device and a processor. The processor is configured to add, to a point cloud representing an anatomical volume, multiple points corresponding to respective locations of a probe within the anatomical volume. The processor is further configured to remove a subset of the points from the point cloud, subsequently to adding the points, in response to an input received via the input device. The processor is further configured to add to the point cloud, subsequently to removing the subset, other points corresponding to respective subsequent locations of the probe within the anatomical volume.

In some embodiments,
the input indicates that the probe is to be used in a point-removal mode, and
the processor is configured to remove the subset by, for each point in the subset, removing the point in response to ascertaining that the probe is at a location to which the point corresponds.

In some embodiments,
the input is a first input, and
the processor is configured to add the other points to the point cloud in response to a second input indicating that the probe is to be used in a point-addition mode.

In some embodiments, the processor is configured to remove the point in response to ascertaining that the probe is pushing against a surface of the anatomical volume.

In some embodiments, the input indicates a period of time, and the subset includes those of the points that were added to the point cloud during the period of time.

In some embodiments, the period of time begins T units of time before a time at which the input is submitted, and the input indicates the period of time by indicating T.

In some embodiments, the input indicates an integer N, and the subset includes N of the points that were most recently added to the point cloud.

In some embodiments, the anatomical volume includes at least part of a chamber of a heart.

There is further provided, in accordance with some embodiments of the present invention, a method including, using a processor, adding, to a point cloud representing an anatomical volume, multiple points corresponding to respective locations of a probe within the anatomical volume. The method further includes, subsequently to adding the points, removing a subset of the points from the point cloud in response to an input from a user. The method further includes, subsequently to removing the subset, adding, to the point cloud, other points corresponding to respective subsequent locations of the probe within the anatomical volume.

There is further provided, in accordance with some embodiments of the present invention, a computer software product including a tangible non-transitory computer-readable medium in which program instructions are stored. The instructions, when read by a processor, cause the processor to add, to a point cloud representing an anatomical volume, multiple points corresponding to respective locations of a probe within the anatomical volume. The instructions further cause the processor to remove a subset of the points from the point cloud in response to an input from a user, subsequently to adding the points. The instructions further cause the processor to add to the point cloud, subsequently to removing the subset, other points corresponding to respective subsequent locations of the probe within the anatomical volume.

BRIEF DESCRIPTION OF THE DRAWINGS

The present invention will be more fully understood from the following detailed description of embodiments thereof, taken together with the drawings, in which.

DETAILED DESCRIPTION OF EMBODIMENTS

Overview

In an anatomical mapping of a chamber of a heart, a physician moves a probe through the chamber while a tracking system tracks the location of the probe. Based on the tracking, a model of the chamber is constructed. The model includes a point cloud, which includes multiple points corresponding to the locations of the probe (typically, of the distal end of the probe) within the chamber, and a surface surrounding the point cloud, which represents the tissue surrounding the chamber. The surface may be associated with electrical properties of the tissue, which may be derived from electrogram signals acquired by the probe at various locations on the tissue.

A challenge, when performing such a mapping, is that spurious points may be added to the model, e.g., due to respiratory movement or excess force applied to the tissue by the probe. Conventionally, these points are removed after the mapping by modifying the surface of the model (e.g., using spline deformation and/or surface interpolation) such that the surface passes through points that are known to correspond to locations on the tissue. (These points, referred to herein as "anchor points," may correspond to those locations at which electrogram signals were acquired, since the physician is generally careful, when acquiring the electrogram signals, not to push against the tissue with excess force.) However, this deformation may compromise the accuracy of the model.

To address this challenge, embodiments of the present invention provide various techniques for removing spurious points from the model. Following the removal of the spurious points, the surface may be regenerated. Thus, it may not be necessary to deform the surface.

Per one such technique, a point-removal mode for operation of the probe is provided. While the probe is operated in this mode, movement of the probe to a particular location causes the points corresponding to this location to be removed from the model. The physician may thus correct the model in real-time, by switching from the usual point-addition mode to the point-removal model, and then moving the probe to any locations that correspond to spurious points.

Per another such technique, for each anchor point, a virtual sphere whose surface passes through the anchor point is defined (as described in detail below with reference to FIG. 4A), and any points within the sphere are then removed from the point cloud. Subsequently, the model surface—or at least the portion of the model surface near the anchor point—is regenerated, such that the model surface passes through the anchor point. Advantageously, this technique may be performed following the acquisition of each new anchor point, during or following the construction of the point cloud.

For cases in which an anchor point lies outside the point cloud, a variation of the latter technique may be performed. Per this variation, following the definition of the virtual sphere, the sphere is filled with additional points so as to augment the point cloud.

System Description

Figure 1:
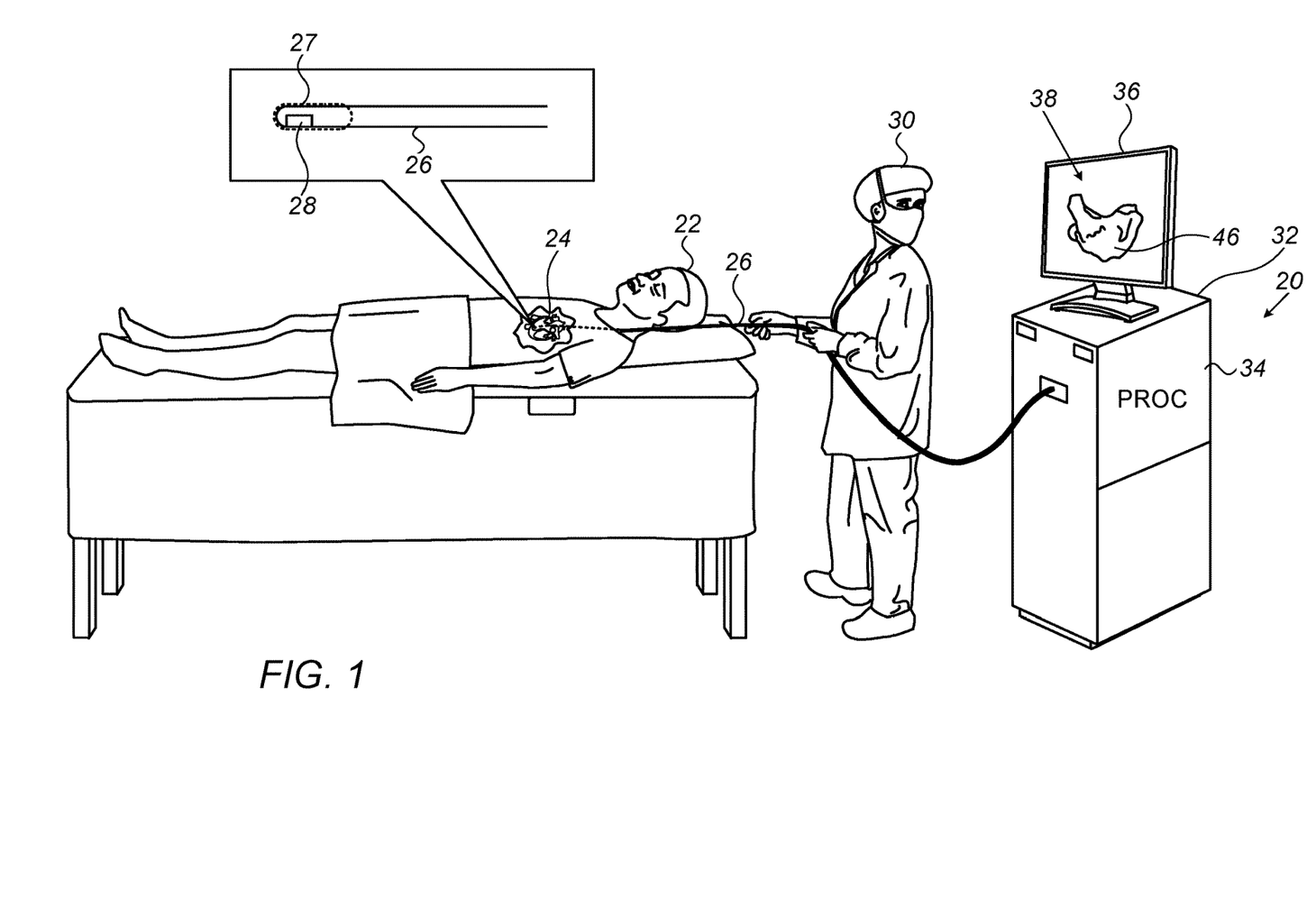
FIG. 1 is a schematic illustration of an anatomical mapping system, in accordance with some exemplary embodiments of the present invention.

Reference is initially made to FIG. 1, which is a schematic illustration of an anatomical mapping system 20, in accordance with some embodiments of the present invention.

System 20 comprises an intrabody probe 26 proximally connected to a console 32. System 20 further comprises a processor 34, which is typically contained in console 32.

System 20 is used to generate an anatomical map 38 of a volume of the heart 24 of a subject 22, such as at least part of a chamber of heart 24. Map 38 includes a point cloud, which represents the mapped volume by virtue of including a plurality of points corresponding to respective locations within the mapped volume. Map 38 further includes a virtual surface 46 around the periphery of the point cloud. While the map is being generated, and/or subsequently to the generation of the map, the processor may display the map on a display 36.

More specifically, as a physician 30 moves probe 26 within the volume, processor 34 continually ascertains the sub-volume 27 occupied by the distal end of the probe. The processor further constructs the point cloud by adding to the point cloud, for each ascertained sub-volume 27, one or more points—typically, multiple points—corresponding to sub-volume 27. (Each added point thus corresponds to a respective location of the probe—in particular, of any portion of the distal end of the probe—within the mapped volume.) Subsequently to constructing the point cloud, and/or intermittently while the point cloud is constructed, the processor generates virtual surface 46. (It is noted that for ease of description, sub-volume 27 may be referred to herein as the "location of the probe.")

Typically, the distal end of probe 26 comprises at least one sensing electrode 28. As the probe is moved within the heart, electrode 28 acquires electrogram signals from tissue of the heart. Processor 34 analyzes these signals and, in response thereto, annotates map 38 (e.g., by coloring the map per a sliding color scale) to indicate electrical properties of the tissue. In such embodiments, map 38 may be referred to as an "electroanatomical map" or an "electrophysiological map."

In some embodiments, to facilitate tracking the probe, one or more electromagnetic coils are coupled to the distal end of the probe, and a magnetic field is generated in the vicinity of subject 22. As the probe is moved within the heart, the magnetic field induces a location-dependent signal in the coils. Based on this signal, the processor ascertains the location of each of the coils, and hence, identifies sub-volume 27. Such magnetic-based tracking is disclosed, for example, in U.S. Pat. Nos. 5,391,199, 5,443,489, and 6,788,967 to Ben-Haim, U.S. Pat. No. 6,690,963 to Ben-Haim et al., U.S. Pat. No. 5,558,091 to Acker et al., and U.S. Pat. No. 6,177,792 to Govari, whose respective disclosures are incorporated herein by reference.

Alternatively or additionally, one or more electrodes coupled to the distal end of the probe may pass electric currents to a plurality of electrode patches coupled to the subject's body at different respective locations. (Typically, these electrodes do not include electrode 28.) Based on the electric currents and the body-impedance measurements derived therefrom, the processor may ascertain the location of each of the electrodes, and hence, identify sub-volume 27. A hybrid technique combining such impedance-based tracking with magnetic-based tracking is described in U.S. Pat. No. 8,456,182 to Bar-Tal et al., whose disclosure is incorporated herein by reference.

Alternatively or additionally, the processor may track the probe, and hence construct the point cloud, using any other suitable tracking technique.

In general, processor 34 may be embodied as a single processor, or as a cooperatively networked or clustered set of processors. In some embodiments, the functionality of processor 34, as described herein, is implemented solely in hardware, e.g., using one or more Application-Specific Integrated Circuits (ASICs) or Field-Programmable Gate Arrays (FPGAs). In other embodiments, the functionality of processor 34 is implemented at least partly in software. For example, in some embodiments, processor 34 is embodied as a programmed digital computing device comprising at least a central processing unit (CPU) and random-access memory (RAM). Program code, including software programs, and/or data are loaded into the RAM for execution and processing by the CPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Generating the Anatomical Map

Figure 2:
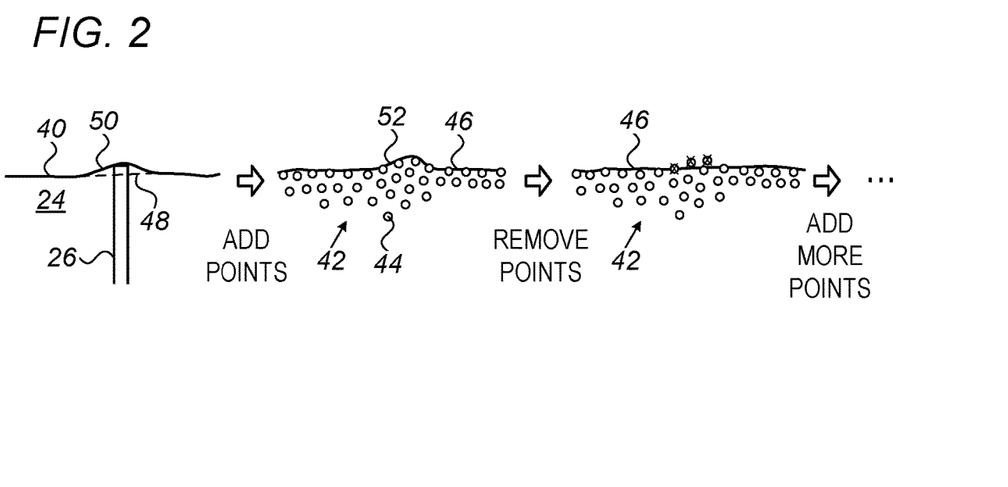
FIG. 2 is a schematic illustration of a technique for generating an anatomical map, in accordance with some exemplary embodiments of the present invention.

Reference is now made to FIG. 2, which is a schematic illustration of a technique for generating map 38, in accordance with some embodiments of the present invention.

FIG. 2 shows a portion of a point cloud 42, which, as described above with reference to FIG. 1, represents the mapped volume of the heart by virtue of including a plurality of points 44 corresponding to respective locations of probe 26 within the heart. FIG. 2 further shows virtual surface 46, which represents the anatomical surface 40 of the mapped volume (i.e., the tissue surrounding the mapped volume).

Typically, the processor generates virtual surface 46 by applying the ball-pivoting algorithm (BPA), described in Bernardini, Fausto, et al., "The ball-pivoting algorithm for surface reconstruction," *IEEE transactions on visualization and computer graphics* 5.4 (1999): 349-359, which is incorporated herein by reference, to the point cloud. This algorithm computes surface 46 as a triangulated mesh that approximately interpolates the points at the periphery of the point cloud, by (i) finding a seed triangle whose vertices are points at the periphery of the point cloud, and then (ii) expanding the triangulation by pivoting a virtual ball around the edges of the existing triangles until no open edges remain. Alternatively, the processor may use any other suitable surface-generating algorithm.

The leftmost portion of FIG. 2 illustrates a scenario in which probe 26 pushes surface 40 outward from the natural position 48 of the surface, so as to create a bulge 50 in the surface. Consequently, as shown in the middle portion of FIG. 2, spurious points, which correspond to one or more locations of the probe within bulge 50, are added to the point cloud, such that virtual surface 46 acquires a spurious bulge 52.

To address this problem, embodiments of the present invention provide various techniques for removing a subset of points 44 from the point cloud and then regenerating virtual surface 46, as shown in the rightmost portion of FIG. 2. Subsequently to the removal of the subset, other points may be added to the point cloud. In this manner, spurious points may be removed during the mapping procedure, thus reducing the required post-processing of the map.

Typically, the removal of the subset of points is initiated by a user of the system. For example, in response to noticing bulge 52 on display 36 (FIG. 1), a user, such as physician 30, may submit an input indicating that some of the points should be removed from the point cloud. Subsequently, in response to the input, the processor may remove the subset of points.

In some embodiments, the probe may be used in two different modes: a point-addition mode, and a point-removal mode. While the probe is in the point-addition mode, the processor adds respective points corresponding to each new location of the probe. On the other hand, while the probe is in the point-removal mode, the processor removes any points corresponding to the location of the probe. (In addition, the probe may have a third, inactive mode, in which points are neither added nor removed.)

In such embodiments, the aforementioned input from the user indicates that the probe is to be used in the point-removal mode, and the processor removes each point in the subset in response to ascertaining that the probe is at a location to which the point corresponds. For example, subsequently to adding a first group of points to the point cloud, the physician may submit an input indicating that the probe is to be used in the point-removal mode. Subsequently, the physician may pass the probe through a previously-mapped portion of the subject's anatomy. In response to the input and to ascertaining the locations of the probe within this portion, the processor may remove the points corresponding to these locations. Next, after removing the probe from this portion, the physician may submit another input indicating that the probe is to be used, again, in the point-addition mode. In response to this input, the processor may again add points to the point cloud.

To reduce the number of legitimate points removed from the point cloud, the processor may, before removing a point, check whether the probe is pushing against surface 40, e.g., by processing a signal from a pressure sensor at the distal end of the probe. In response to ascertaining that the probe is pushing against the surface, the processor may remove the point; otherwise, the processor may refrain from removing the point.

Alternatively or additionally to operating the probe in a point-removal mode, other techniques may be used to remove points from the point cloud. For example, the point-removal-initiating input from the user may indicate a period of time, and the removed subset of points may include those of the points that were added to the point cloud during the period of time. As a specific example, the period of time may begin T units of time (e.g., seconds) before the time at which the input is submitted, and the input may indicate the period of time by indicating T. Alternatively, the input may indicate an integer N, and the subset may include the N points that were most recently added to the point cloud.

In general, the user may use any suitable input device to submit the aforementioned inputs. For example, the user may press one or more buttons or keys on console 32 (FIG. 1) or on a control handle for the probe. Alternatively or additionally, the display may comprise a touch screen, and the user may submit at least some of the inputs via the touch screen. Alternatively or additionally, the user may submit at least some of the inputs using a keyboard and/or mouse. As yet another option, the user may use a foot pedal, e.g., to toggle between the modes in which the probe is operated.

Figure 3:
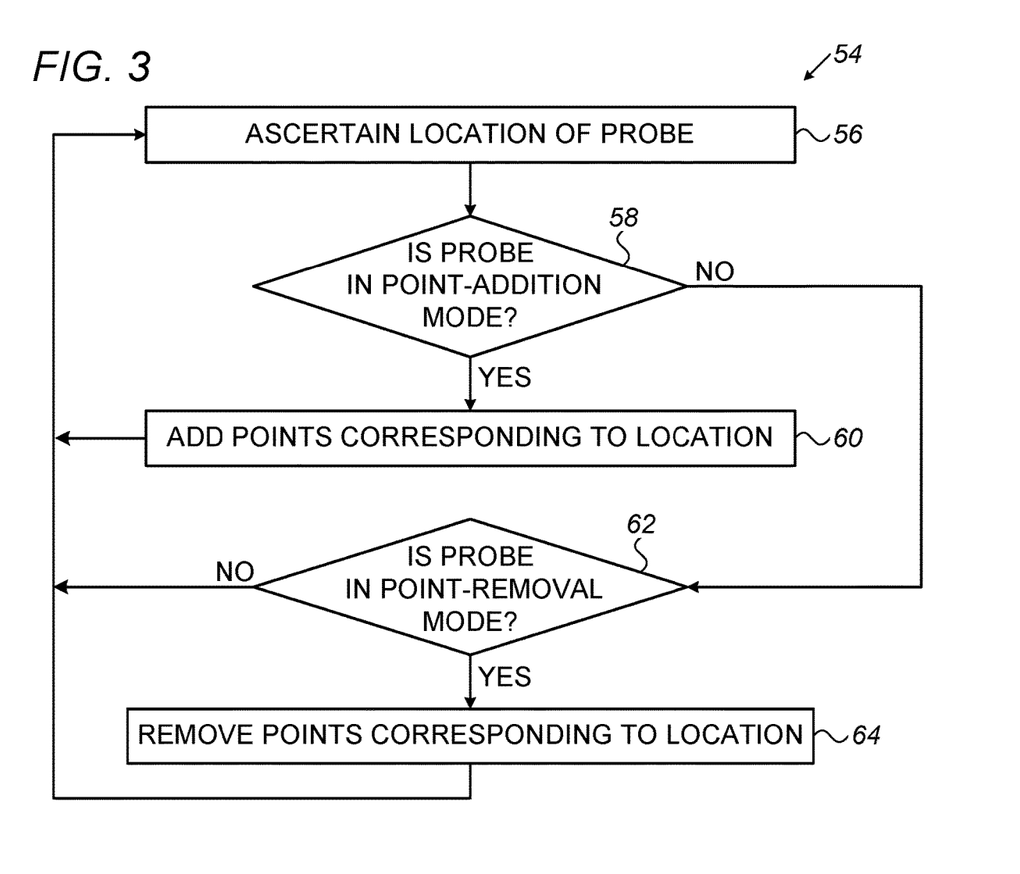
FIG. 3 is a flow diagram for an algorithm for generating an anatomical map, in accordance with some exemplary embodiments of the present invention.

Reference is now made to FIG. 3, which is a flow diagram for an algorithm 54 for generating map 38 (FIG. 1), in accordance with some embodiments of the present invention.

Per algorithm 54, the processor repeatedly ascertains the location of the probe at a location-ascertaining step 56. Subsequently to ascertaining the location of the probe, the processor checks, at a first checking step 58, whether the probe is in the point-addition mode. If yes, the processor adds, to the point cloud, one or more points corresponding to the location, at a point-adding step 60. Otherwise, the processor checks, at a second checking step 62, whether the probe is in the point-removal mode. If yes, the processor removes one or more points corresponding to the location, at a point-removing step 64. Subsequently to adding or removing points, or if the probe is neither in the point-addition mode nor in the point-removal mode (but rather, is in the inactive mode), the processor returns to location-ascertaining step 56.

In parallel to algorithm 54, the processor may execute another algorithm for receiving input from the user and toggling between the modes in response thereto. Additionally, in parallel to algorithm 54, the processor may execute another algorithm for intermittently regenerating virtual surface 46 (FIG. 2). For example, the processor may intermittently regenerate part of the virtual surface at each peripheral portion of the point cloud at which points have been added or removed.

Using the Anchor Points

In some embodiments, the processor identifies one or more anchor points known to correspond to locations on the anatomical surface. For each anchor point, the processor may remove a portion of the point cloud lying outside the anchor point, and then regenerate the virtual surface such that the virtual surface passes through the anchor point. (This technique may be performed alternatively or additionally to the point-removal techniques described above.) Alternatively, the processor may expand the point cloud such that, following the regeneration of the virtual surface, the virtual surface passes through the anchor point.

Typically, the processor identifies each anchor point in response to an input from a user, such as physician 30 (FIG. 1). For example, as described above in the Overview, during the mapping, electrogram signals may be acquired at various locations on the anatomical surface. At each of these locations, the physician may place the probe in contact with the tissue, typically without pushing the tissue outward, and then submit an input to the processor indicating that the probe is located on the tissue. (In general, the user may use any suitable input device to submit this input, as described above with reference to FIG. 2.) In response to such an input, the processor may identify, as an anchor point, a point corresponding to the location of the probe. (It is noted that the anchor point may already belong to the point cloud, by virtue of the probe having previously been at the current location.) Alternatively or additionally, while the point cloud is displayed on display 36 (FIG. 1), the user may select, as the anchor point, one of the points belonging to the point cloud, e.g., using a touch screen or mouse to perform this selection.

Figure 4A:
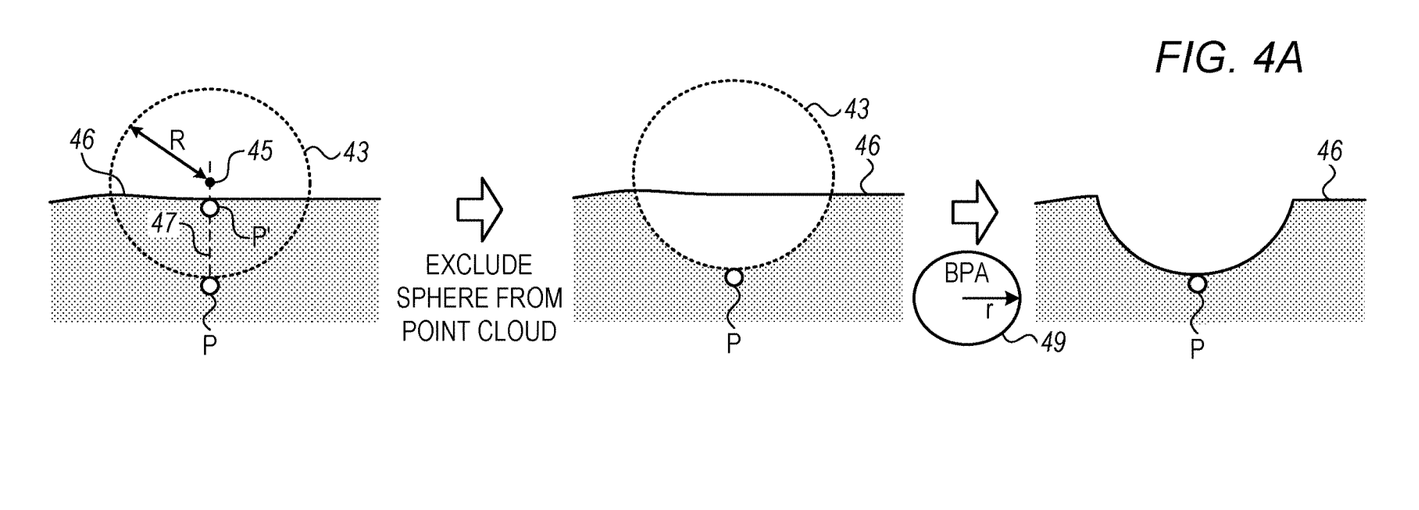
FIGS. 4A-B are schematic illustrations of a technique for reconstructing a model, in accordance with some exemplary embodiments of the present invention.
Figure 4B:
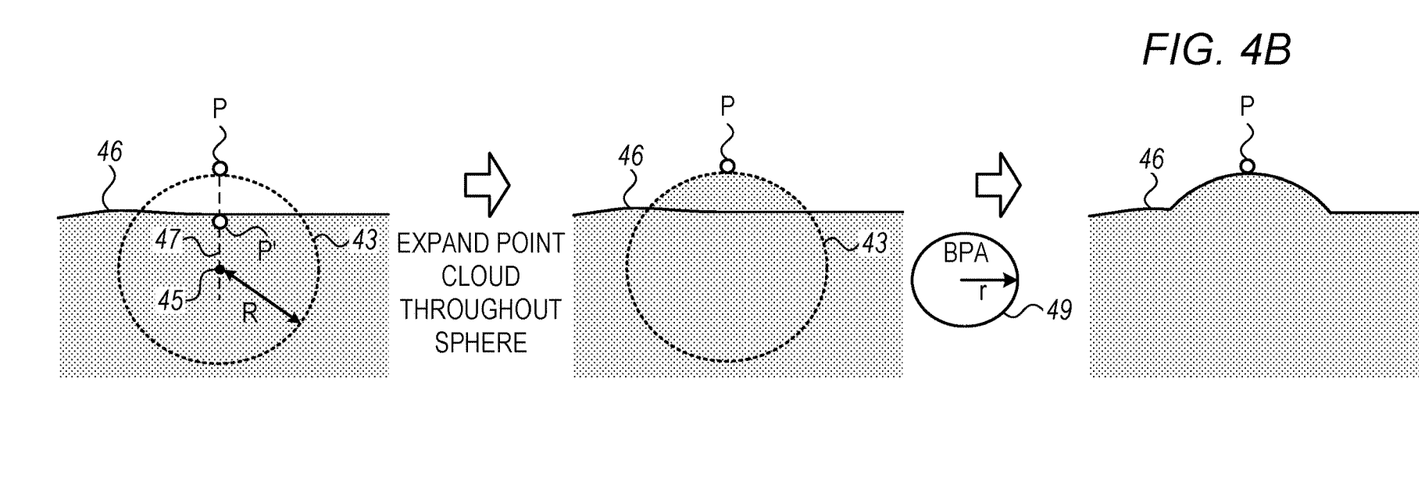

For further details, reference is now made to FIGS. 4A-B, which are schematic illustrations of a technique for reconstructing a model, in accordance with some embodiments of the present invention.

The leftmost portion of FIG. 4A illustrates a scenario in which the point cloud, and hence virtual surface 46, have been erroneously expanded outward. (The shaded portions of FIGS. 4A-B correspond to the point cloud.) In this scenario, the processor, as shown in the middle portion of FIG. 4A, removes points from the point cloud such that an anchor point P, which corresponds to a location on the anatomical surface, is at the periphery of the point cloud. Subsequently, as shown in the rightmost portion of FIG. 4A, the processor regenerates virtual surface 46 such that, by virtue of P being at the periphery of the point cloud, P lies on the virtual surface.

In particular, subsequently to identifying point P, the processor computes another point P' on the virtual surface, by projecting P onto the virtual surface. In other words, the processor computes P' as the point on the virtual surface closest to P. (P' may be an original point belonging to the point cloud, though typically P' is a new point defined by the processor.) Subsequently, the processor defines a virtual sphere 43 centered on (i.e., having a center 45 that lies on) a virtual line 47 joining P to P' such that P lies on the (spherical) surface of virtual sphere 43. Next, the processor excludes the virtual sphere from the point cloud, i.e., the processor removes, from the point cloud, each point lying within the sphere. Finally, the processor regenerates the virtual surface such that, by virtue of having excluded the virtual sphere from the point cloud, P lies on the virtual surface.

Typically, the virtual surface is regenerated using the BPA. In such embodiments, the radius R of the sphere is at least 2r, r being the radius of the virtual ball 49 used for the BPA, such that ball 49 may be pivoted within the region from which the points were removed. For example, R may equal 2r.

As illustrated in FIG. 4B, the above-described technique may also be used to advance the point cloud and virtual surface outward, in the event that a peripheral portion of the anatomical volume was missed during the mapping. In other words, the processor may identify P' and then define the virtual sphere, as described above and shown in the leftmost portion of FIG. 4B. Subsequently, the processor may expand the point cloud throughout the virtual sphere, i.e., fill the portion of the sphere lying outside the point cloud with new points, as shown in the middle portion of FIG. 4B. (The new points may have any suitable inter-point spacing.) Finally, as shown in the rightmost portion of FIG. 4B, the processor may regenerate the virtual surface as described above, such that, by virtue of having expanded the point cloud throughout the virtual sphere, P lies on the virtual surface.

Figure 5:
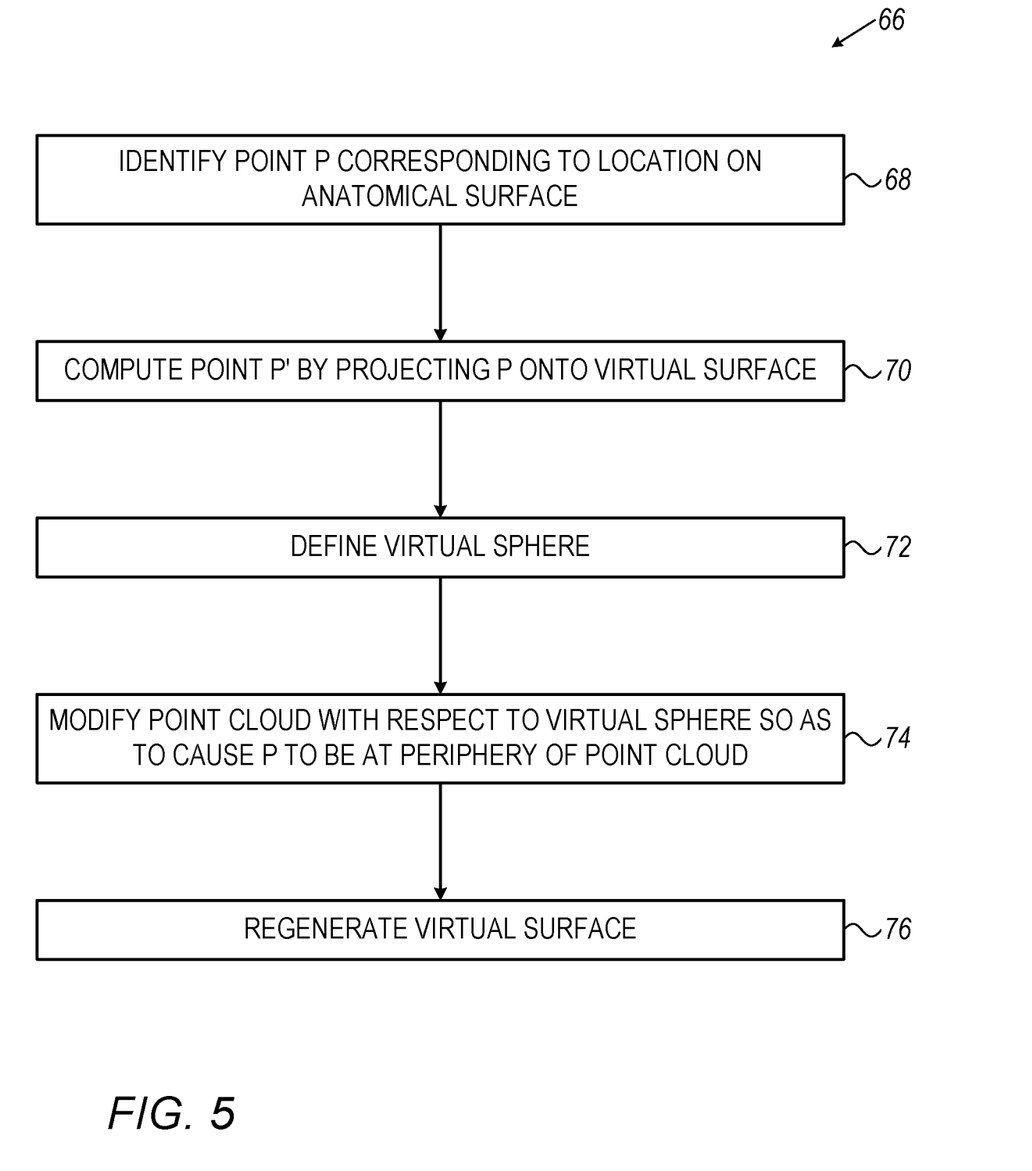
FIG. 5 is a flow diagram for an algorithm for reconstructing a model, in accordance with some exemplary embodiments of the present invention.

Reference is now made to FIG. 5, which is a flow diagram for an algorithm 66 for reconstructing a model, in accordance with some embodiments of the present invention.

Algorithm 66 begins with a point-identifying step 68, at which the processor identifies the anchor point P. Subsequently, at a projecting step 70, the processor computes point P' by projecting P onto the virtual surface. Next, at a virtual-sphere-defining step 72, the processor defines the virtual sphere. Following the definition of the virtual sphere, the processor, at a point-cloud-modifying step 74, modifies the point cloud with respect to the virtual sphere (by adding points to, or removing points from, the virtual sphere) so as to cause P to be at the periphery of the point cloud. Finally, at a regenerating step 76, the processor regenerates the virtual surface such that, subsequently, P lies on the virtual surface.

Although the above description mainly relates to the mapping of a chamber of a heart, it is noted that the techniques described herein may also be applied to the mapping of any other anatomical volume, such as an otolaryngological volume.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for anatomical mapping, the system comprising:
   a display; and
   a processor, configured to:
      compute a point P' on a virtual surface of a point cloud representing an anatomical volume, by projecting another point P, which corresponds to a location on an anatomical surface of the anatomical volume, onto the virtual surface,
      define a virtual sphere centered on a virtual line joining P to P' such that P lies on a spherical surface of the virtual sphere,
      perform an operation selected from the group of operations consisting of: expanding the point cloud throughout the virtual sphere, and excluding the virtual sphere from the point cloud,
      subsequently to performing the operation, regenerate the virtual surface such that, by virtue of having performed the operation, P lies on the virtual surface, and
      display the regenerated virtual surface on the display.

2. The system according to claim 1, wherein the processor is configured to regenerate the virtual surface by applying a ball-pivoting algorithm (BPA) with a ball radius r to the point cloud, and wherein the processor is configured to define the sphere such that a radius R of the sphere is at least 2r.

3. The system according to claim 2, wherein R=2r.

4. The system according to claim 1, wherein the processor is further configured to identify P in response to an input from a user.

5. The system according to claim 4, wherein the input indicates that an intrabody probe is at the location.

6. The system according to claim 4, wherein the input includes a selection of P from a display of the point cloud.

7. The system according to claim 1, wherein the anatomical volume includes at least part of a chamber of a heart.

8. A method for anatomical mapping, the method comprising:
   using a processor, computing a point P' on a virtual surface of a point cloud representing an anatomical volume, by projecting another point P, which corresponds to a location on an anatomical surface of the anatomical volume, onto the virtual surface;
   defining a virtual sphere centered on a virtual line joining P to P' such that P lies on a spherical surface of the virtual sphere;
   performing an operation selected from the group of operations consisting of: expanding the point cloud throughout the virtual sphere, and excluding the virtual sphere from the point cloud; and
   subsequently to performing the operation, regenerating the virtual surface such that, by virtue of having performed the operation, P lies on the virtual surface.

9. The method according to claim 8, wherein regenerating the virtual surface comprises regenerating the virtual surface by applying a ball-pivoting algorithm (BPA) with a ball radius r to the point cloud, and wherein defining the sphere comprises defining the sphere such that a radius R of the sphere is at least 2r.

10. The method according to claim 9, wherein R=2r.

11. The method according to claim 8, further comprising identifying P in response to an input from a user.

12. The method according to claim 11, wherein the input indicates that an intrabody probe is at the location.

13. The method according to claim 11, wherein the input includes a selection of P from a display of the point cloud.

14. The method according to claim 8, wherein the anatomical volume includes at least part of a chamber of a heart.

15. A computer software product comprising a tangible non-transitory computer-readable medium in which program instructions are stored, which instructions, when read by a processor, cause the processor to:
   compute a point P' on a virtual surface of a point cloud representing an anatomical volume, by projecting another point P, which corresponds to a location on an anatomical surface of the anatomical volume, onto the virtual surface,
   define a virtual sphere centered on a virtual line joining P to P' such that P lies on a spherical surface of the virtual sphere, perform an operation selected from the group of operations consisting of: expanding the point cloud throughout the virtual sphere, and excluding the virtual sphere from the point cloud, and subsequently to performing the operation, regenerate the virtual surface such that, by virtue of having performed the operation, P lies on the virtual surface.

16. The computer software product according to claim 15, wherein the instructions cause the processor to regenerate the virtual surface by applying a ball-pivoting algorithm (BPA) with a ball radius r to the point cloud, and wherein the instructions cause the processor to define the sphere such that a radius R of the sphere is at least 2r.

17. The computer software product according to claim 15, wherein the instructions further cause the processor to identify P in response to an input from a user.

18. The computer software product according to claim 17, wherein the input indicates that an intrabody probe is at the location.

19. The computer software product according to claim 17, wherein the input includes a selection of P from a display of the point cloud.

20. The computer software product according to claim 15, wherein the anatomical volume includes at least part of a chamber of a heart.

* * * * *